(12) United States Patent
Walsworth et al.

(10) Patent No.: US 12,276,624 B2
(45) Date of Patent: Apr. 15, 2025

(54) SYSTEMS AND METHODS FOR QUANTUM SENSING WITH SIGNAL AMPLIFICATION BY REVERSIBLE EXCHANGE

(71) Applicants: University of Maryland, College Park, College Park, MD (US); The President and Fellows of Harvard College, Cambridge, MA (US); North Carolina State University, Raleigh, NC (US)

(72) Inventors: Ronald Walsworth, Newton, MA (US); Nithya Arunkumar, Waltham, MA (US); Dominik Bucher, Puchheim (DE); Matthew Turner, Cambridge, MA (US); David Glenn, Cambridge, MA (US); Matthew S. Rosen, Somerville, MA (US); Thomas Theis, Durham, NC (US)

(73) Assignees: University of Maryland, College Park, College Park, MD (US); The President and Fellows of Harvard College, Cambridge, MA (US); North Carolina State University, Raleigh, NC (US)

( * ) Notice: Subject to any disclaimer, the term of this patent is extended or adjusted under 35 U.S.C. 154(b) by 279 days.

(21) Appl. No.: 17/829,565

(22) Filed: Jun. 1, 2022

(65) Prior Publication Data

US 2023/0081886 A1 Mar. 16, 2023

Related U.S. Application Data

(60) Provisional application No. 63/197,309, filed on Jun. 4, 2021, provisional application No. 63/195,591, filed on Jun. 1, 2021.

(51) Int. Cl.
*G01N 24/00* (2006.01)
*G01N 24/08* (2006.01)
*G01N 33/00* (2006.01)

(52) U.S. Cl.
CPC .......... *G01N 24/006* (2013.01); *G01N 24/08* (2013.01); *G01N 33/389* (2024.05)

(58) Field of Classification Search
CPC .... G01N 24/006; G01N 24/08; G01N 33/389; G01R 33/032; G01R 33/26; G01R 33/323
See application file for complete search history.

(56) References Cited

U.S. PATENT DOCUMENTS 10,914,800 B2 2/2021 Acosta et al.
2014/0327439 A1 11/2014 Cappellaro et al.
(Continued)

OTHER PUBLICATIONS

Glenn et al., "High-Resolution Magnetic Resonance Spectroscopy Using a Solid-State Spin Sensor", Nature, vol. 555, Mar. 15, 2018, pp. 351-364.
(Continued)

*Primary Examiner* — G. M. A Hyder
(74) *Attorney, Agent, or Firm* — Carter, DeLuca & Farrell LLP; George Likourezos

(57) ABSTRACT

Systems and methods of quantum sensing include depositing a sample volume onto an ensemble of quantum defects, hyperpolarizing spins in the sample volume, performing a sensing sequence, and reading out information regarding electronic spin states of the quantum defects in the ensemble of quantum defects, which sense the hyperpolarized spins in the sample volume.

28 Claims, 6 Drawing Sheets

(56) References Cited

U.S. PATENT DOCUMENTS

2015/0009746 A1 1/2015 Kucsko et al.
2015/0090033 A1 4/2015 Budker et al.
2017/0153218 A1* 6/2017 Chekmenev ......... G01R 33/282

OTHER PUBLICATIONS

Bucher et al., "Hyperpolarization-Enhanced NMR Spectroscopy with Femtomole Sensitivity Using Quantum Defects in Diamond", Physical Review X 10, 021053 (2020), 9 pages.
Adams et al., "Reversible Interactions with para-Hydrogen Enhance NMR Sensitivity by Polarization Transfer", Science, vol. 323, Mar. 27, 2009, pp. 1708-1711.
Cowley et al., "Iridium N-Heterocyclic Carbene Complexes as Efficient Catalysts for Magnetization Transfer from para-Hydrogen", Journal of the American Chemical Society, vol. 133, Apr. 6, 2011, pp. 6134-6137.
Theis et al., "Zero-Field NMR Enhanced by Parahydrogen in Reversible Exchange", Journal of the American Chemical Society, vol. 134, Feb. 14, 2012, pp. 3987-3990.
Smits et al., "Two-Dimensional Nuclear Magnetic Resonance Spectroscopy with a Microfluidic Diamond Quantum Sensor", Science Advances, vol. 5, Jul. 26, 2019, 7 pages.
Rayner et al., "Signal Amplification by Reversible Exchange (SABRE): From Discovery to Diagnosis", Angew. Chem. Int. Ed., vol. 57, 2018, pp. 6742-6753.
Jiang et al., "Repetitive Readout of a Single Electronic Spin via Quantum Logic with Nuclear Spin Ancillae", Science, vol. 326, Oct. 9, 2009, pp. 267-272.
Neumann et al., "Single-Shot Readout of a Single Nuclear Spin", Science, vol. 329, Jul. 30, 2010, pp. 542-544.
Lovchinsky et al., "Nuclear Magnetic Resonance Detection and Spectroscopy of Single Proteins Using Quantum Logic", Science, vol. 351, Feb. 19, 2016, pp. 836-841.
Zhou et al., "Quantum Metrology with Strongly Interacting Spin Systems", Physical Review X 10, 031003 (2020), 9 pages.
Choi et al., "Robust Dynamic Hamiltonian Engineering of Many-Body Spin Systems", Physical Review X 10, 031002 (2020), 27 pages.
Taylor et al., "High-sensitivity diamond magnetometer with nanoscale resolution", Nature Physics vol. 4, Oct. 2008, pp. 810-816.
John F. Barry, "Sensitivity optimization for NV-diamond magnetometry", Rev. Mod. Phys., vol. 92, No. 1, Published Mar. 31, 2020, pp. 015004 -1 to 015004-68.
Staudacher et al., Nuclear Magnetic Resonance Spectroscopy on a (5-Nanometer)3 Sample vol. Science, vol. 339, Feb. 1, 2013, pp. 561-563.
Mamin et al., "Nanoscale Nuclear Magnetic Resonance with a Nitrogen-Vacancy Spin Sensor", Science, vol. 339, Feb. 1, 2013, pp. 557-560.
Müller et al., "Nuclear magnetic resonance spectroscopy with single spin sensitivity", Nature Communications, vol. 5, 4703, Aug. 2014, pp. 1-6.
Sushkov et al., "Magnetic Resonance Detection of Individual Proton Spins Using Quantum Reporters", Physical Review Letters, vol. 113, Nov. 7, 2014, pp. 197601-1-197601-5.
Aslam et al., "Nanoscale nuclear magnetic resonance with chemical resolution", Science, vol. 357, Jul. 7, 2017, pp. 67-71.
Glenn et al., "High-resolution magnetic resonance spectroscopy using a solid-state spin sensor", Nature, vol. 555, Mar. 15, 2018, 14 pages.
Bucher et al., "Hyperpolarization-Enhanced NMR Spectroscopy with Femtomole Sensitivity Using Quantum Defects in Diamond", Phys. Rev. X 10, 2020, pp. 021053-1-021053-9.
Rayner et al., "Delivering strong 1H nuclear hyperpolarization levels and long magnetic lifetimes through signal amplification by reversible exchange", PNAS, Apr. 4, 2017, pp. E3188-3194.
Theis et al., "Zero-field NMR enhanced by parahydrogen in reversible exchange", J Am Chem Soc, 2012, 134, 9, pp. 3987-3990.
Gong et al., "Trace Analysis by Low-Field NMR: Breaking the Sensitivity Limit", Analytical Chemistry, vol. 82, No. 17, Sep. 1, 2010, pp. 7078-7082.
Theis et al., "Microtesla SABRE Enables 10% Nitrogen-15 Nuclear Spin Polarization", J. Am. Chem. Soc. 2015, 137, pp. 1404-1407.
Bucher et al., "Quantum diamond spectrometer for nanoscale NMR and ESR spectroscopy", Nature Protocols, vol. 14, Sep. 2019, pp. 2707-2747.
Badilita et al., "Microscale nuclear magnetic resonance: a tool for soft matter research", Soft Matter, 2012, vol. 8, pp. 10583-10597.
Colell et al., "Generalizing, Extending, and Maximizing Nitrogen-15 Hyperpolarization Induced by Parahydrogen in Reversible Exchange", J. Phys. Chem. C 2017, 121, pp. 6626-6634.
Troung et al., "15N Hyperpolarization by Reversible Exchange Using Sabre-Sheath", J. Phys. Chem. C, 2015, vol. 119, pp. 8786-8797.
Lehmkuhl et al., "SABRE polarized low field rare-spin spectroscopy", J. Chem. Phys. 152, 2020, pp. 184202-1-184202-9.
Canto et al., "The NAD+ Precursor Nicotinamide Riboside Enhances Oxidative Metabolism and Protects against High-Fat Diet-Induced Obesity", Cell Metabolism, vol. 15, Jun. 6, 2012, pp. 838-847.
Knecht et al., "Re-polarization of nuclear spins using selective SABRE-INEPT", Journal of Magnetic Resonance 287, 2018, pp. 10-14.
Atkinson et al., "Para-Hydrogen Induced Polarization without Incorporation of Para-Hydrogen into the Analyte", Inorganic Chemistry, 2009, vol. 48, No. 2, pp. 663-670.
Theis et al., "LIGHT-SABRE enables efficient in-magnet catalytic hyperpolarization", Journal of Magnetic Resonance, vol. 248, 2014, pp. 23-26.
Roy et al., "Direct enhancement of nitrogen-15 targets at high-field by fast ADAPT-SABRE", Journal of Magnetic Resonance, vol. 285, pp. 2017 55-60.
Svyatova et al., "15N Mri of SLIC-SABRE Hyperpolarized 15N-Labelled Pyridine and Nicotinamide", Chemistry A European Journal, 2019, vol. 25, pp. 8465-8470.
Pravdivtsev et al., "RF-SABRE: A Way to Continuous Spin Hyperpolarization at High Magnetic Fields", The Journal of Physical Chemistry B, 2015, vol. 119, pp. 13619-13629.
Theis et al., "Quasi-Resonance Signal Amplification by Reversible Exchange", The Journal of Physical Chemistry Letters, 2018, vol. 9, pp. 6136-6142.
Ariyasingha et al., "Quasi-Resonance Fluorine-19 Signal Amplification by Reversible Exchange", The Journal of Physical Chemistry Letters, 2019, vol. 10, pp. 4229-4236.
Bordonali et al., "Parahydrogen based NMR hyperpolarisation goes micro: an alveolus for small molecule Chemosensing", Lab Chip, 2019, vol. 19, pp. 503-512.
Smits et al., "Two-dimensional nuclear magnetic resonance spectroscopy with a microfluidic diamond quantum sensor", Science Advances, Jul. 26, 2019, vol. 5: eaaw7895, 7 pages.
Rayner et al., "Signal Amplification by Reversible Exchange (SABRE): From Discovery to Diagnosis", Angew. Chem. Int. Ed., 2018, vol. 57, pp. 6742-6753.
Lali et al., "Using parahydrogen to hyperpolarize amines, amides, carboxylic acids, alcohols, phosphates, and carbonates", Science Advances, Jan. 5, 2018, vol. 4, eaao6250, 6 pages.

* cited by examiner

SYSTEMS AND METHODS FOR QUANTUM SENSING WITH SIGNAL AMPLIFICATION BY REVERSIBLE EXCHANGE

CROSS-REFERENCE TO RELATED APPLICATION

This application claims the benefit of and priority to U.S. Provisional Patent Application Ser. Nos. 63/195,591 (filed on Jun. 1, 2021) and 63/197,309 (filed on Jun. 4, 2021), the entire contents of which are hereby incorporated by reference herein. This application also incorporates by reference, in its entirety, U.S. patent application Ser. No. 17/829,551, filed Jun. 1, 2022 and now U.S. Pat. No. 11,940,399, which claims the benefit of and priority to U.S. Provisional Patent Application Ser. Nos. 63/195,591 and 63/197,309.

STATEMENT REGARDING FEDERALLY SPONSORED RESEARCH/DEVELOPMENT

This invention was made with government support under W911NF-19-2-0181, and W911NF-15-1-0548 awarded by the Army Research Laboratory—Army Research Office. The government has certain rights in the invention.

FIELD

The present disclosure relates to quantum sensing and, more specifically, to systems, methods, and devices for quantum nuclear magnetic resonance (NMR) sensing with signal amplification by reversible exchange (SABRE).

BACKGROUND

Nuclear magnetic resonance (NMR) sensing is a widely used tool for chemical analysis and molecular structure determination. A conventional NMR apparatus uses large sample volumes of about a milliliter.

Nitrogen-vacancy (NV) center quantum defects in diamond are a promising modality for sensitive magnetometry with high spatial-resolution and operation under ambient conditions, including for NMR sensing at small length scales (nanometers to microns). However, initial work on NV center NMR sensors has suffered from low spectral resolution due to the short decoherence time of an NV center.

SUMMARY

Provided in accordance with aspects of the present disclosure is a method of quantum sensing including depositing a sample volume onto an ensemble of quantum defects, hyperpolarizing spins in the sample volume, performing a sensing sequence, and reading out information regarding electronic spin states of the quantum defects in the ensemble of quantum defects, which sense the hyperpolarized spins in the sample volume.

In an aspect of the present disclosure, the method further includes preparing the sample volume by introducing a catalyst into the sample volume. The method may also include dispersing parahydrogen into the sample volume to activate the catalyst and, further still, may include performing parahydrogen bubbling. The parahydrogen bubbling hyperpolarizes the spins in the sample volume.

In another aspect of the present disclosure, hyperpolarizing the spins includes performing signal amplification by reversible exchange (SABRE).

In still another aspect of the present disclosure, the method further includes applying a magnetic bias field to the ensemble of quantum defects.

In yet another aspect of the present disclosure, the method further includes applying a radio frequency (RF) pulse to the ensemble of quantum defects after hyperpolarizing the spins and before performing the sensing sequence. The RF pulse may be a $\pi/2$ RF pulse. In aspects, a wait time is implemented after hyperpolarizing the spins and before applying the RF pulse.

In still yet another aspect of the present disclosure, performing the sensing sequence includes performing a coherently averaged synchronized readout (CASR) sequence.

In another aspect of the present disclosure, reading out the information regarding electronic spin states includes reading out a population difference of the electronic spin states.

In yet another aspect of the present disclosure, the ensemble of quantum defects includes a plurality of nitrogen vacancy (NV) centers in diamond.

In still another aspect of the present disclosure, the method further includes repeating, a plurality of times: hyperpolarizing the spins in the sample volume, performing the sensing sequence, and reading out the information regarding the electronic spin states.

In another aspect of the present disclosure, the method further includes implementing a wait time after reading out the information regarding the electronic spin states and before repeating hyperpolarizing the spins in the sample volume.

In still yet another aspect of the present disclosure, after reading out the information regarding electronic spin states, the method further includes re-initializing the electronic spin states of the quantum defects.

In another aspect of the present disclosure, re-initializing includes applying an optical re-initialization pulse to the ensemble of quantum defects.

A quantum sensing system provided in accordance with aspects of the present disclosure includes an ensemble of quantum defects configured to receive a sample volume thereon, a tube configured to deliver parahydrogen to the sample volume to hyperpolarize spins in the sample volume, a laser source configured to deliver a sensing sequence of light pulses to the ensemble of quantum defects, and a sensor configured to read out information regarding electronic spin states of the quantum defects in the ensemble of quantum defects, which sense the hyperpolarized spins in the sample volume.

In an aspect of the present disclosure, the system further includes an antenna configured to deliver radio frequency (RF) pulses to the ensemble of quantum defects.

In another aspect of the present disclosure, the ensemble of quantum defects includes a plurality of nitrogen vacancy (NV) centers in diamond.

In still another aspect of the present disclosure, the system further includes a controller including at least one processor and at least one associated memory storing instructions to be executed by the at least one processor to cause the at least one controller to repeatedly: direct the delivery of parahydrogen to the sample volume via the tube; direct the laser source to deliver the sensing sequence of light pulses to the ensemble of quantum defects; and obtain, from the sensor, the read out information regarding the electronic spin states of the quantum defects in the ensemble of quantum defects.

To the extent consistent, any of the aspects and/or features detailed herein may be used in conjunction with any or all of the other aspects and/or features described herein.

BRIEF DESCRIPTION OF THE DRAWINGS

Various aspects and features of the present disclosure are described hereinbelow with reference to the drawings wherein.

DETAILED DESCRIPTION

The present disclosure provides systems and methods for quantum nuclear magnetic resonance (NMR) sensing using solid-state spin ensembles, e.g., nitrogen-vacancy (NV) center ensembles in diamond. More specifically, the aspects and features of the present disclosure enable an increase in NV-NMR concentration sensitivity by hyperpolarizing sample proton spins (and/or any other ½ nucleus spins such as, for example, nitrogen-15, carbon-13, fluorine-19, phosphorous-31, etc.) through signal amplification by reversible exchange (SABRE) prior to sensing and readout. Additionally, sensitivity is increased by implementation of a coherently averaged synchronized readout (CASR) technique. The increased sensitivity enabled by the present disclosure allows for micron-scale quantum NMR sensing of small-molecule sample concentrations as low as 1 millimolar at a sensing volume of 10 picoliters. Thus, for example, the aspects and features of the present disclosure enable detection and chemical analysis of low-concentration molecules and their dynamics in complex micron-scale systems such as single cells.

Figure 1:
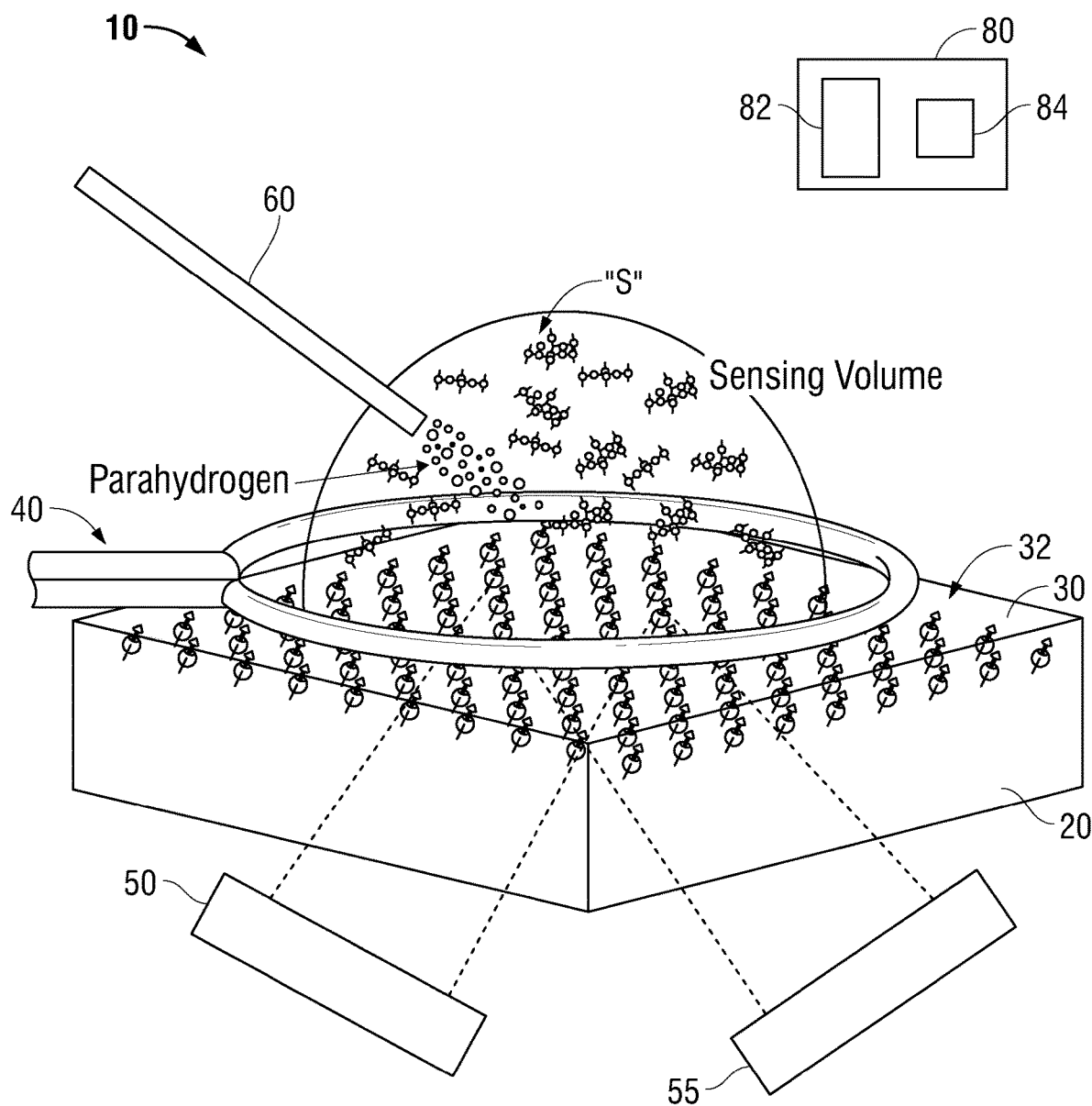
FIG. 1 is a schematic illustration of a nitrogen-vacancy (NV) center ensemble quantum nuclear magnetic resonance (NMR) sensor system in accordance with aspects of the present disclosure.

Turning to FIG. 1, a quantum NV-NMR sensor system 10 provided in accordance with the present disclosure includes a diamond chip 20 (e.g., a 2×2×0.5 $mm^3$ diamond chip 20) having an NV center ensemble layer 30 (e.g., formed via chemical vapor deposition, irradiation, and annealing, or in any other suitable manner). The NV center ensemble layer 30 may define a thickness of 13 μm (or any other suitable thickness) and includes a plurality of NV centers 32. The plurality of NV centers 32 may define a concentration of $3 \times 10^{17}$ $mm^{-3}$, within (plus or minus) an order of magnitude thereof, or any other suitable concentration. The number of NV centers 32 may be at least on the order of $10^4$ in aspects; in other aspects, at least on the order of $10^6$; in still other aspects, at least on the order of $10^8$.

An external magnetic bias field, e.g., an external DC magnetic bias field, is applied to system 10 along the NV symmetry axis. The external magnetic bias field may be generated by a feedback-stabilized electromagnet or in any other suitable manner.

System 10 further includes an antenna 40 configured to deliver microwave (MW) and/or radio frequency (RF) pulse signals. Antenna 40 is shown as a shorted single-loop coil (e.g., of 1 mm diameter) although other suitable antennae for MW and/or RF pulse signal delivery are also contemplated. In aspects, antenna 40 is configured to deliver both MW and RF pulse signals, although separate antennae for MW and RF pulse signal delivery are also contemplated as is only one of an MW or RF antenna.

Figure 2:
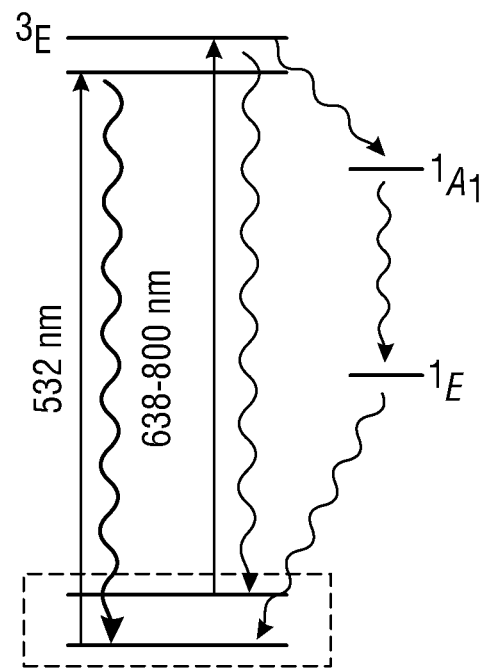
FIG. 2 is an energy level diagram for NV centers in diamond.
Figure 3:
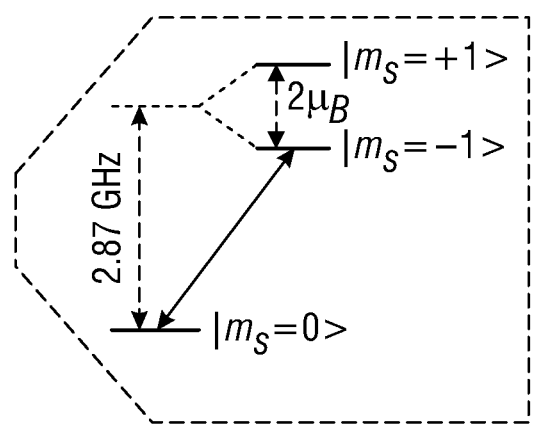
FIG. 3 is an enlarged illustration of the area of detail indicated in FIG. 2.

System 10 also includes a laser source 50 configured to deliver a light pulse to initialize, e.g., polarize, the electronic spin states of the NV centers 32 in the ensemble layer 30 (see also FIGS. 2 and 3) and/or to readout the electronic spins thereof. Laser source 50 is arranged to deliver the light pulse in a total internal reflection configuration (although other configurations are also contemplated) and/or may define a spot diameter of approximately 15 μm. The optical or light pulse may have a wavelength of 532 nm; alternatively, any other suitable wavelength of from about 500 nm to about 637 nm is contemplated, as wavelengths in this range are sufficient to repolarize the NV centers 32 into the ms=0 electronic ground state within <5 ms (typically about 3-7 μs).

A fluorescence sensor 55 of system 10 is configured to optically measure (readout) the electronic spin states of the NV centers 32 in the ensemble layer 30 (see also FIGS. 2 and 3) (and/or the population difference of the electronic spin states), from which a magnetic field can be determined, thus enabling NMR sensing.

The liquid sample volume under test "S" is disposed, e.g., directly, on the NV center ensemble layer 30 of the diamond chip 20. A capillary tube 60 of system 10 is provided to enable diffusion of parahydrogen into the sample volume under test "S."

System 10 may further include at least one controller 80 having at least one processor 82, e.g., at least one quantum processor, and associated memory(s) 84, e.g., quantum memory(s), storing instructions to be executed by the processor(s) 82 to control application of the MW and/or RF pulses, optical polarization pulses, optical readout pulses, the bias magnetic field, and/or the diffusion of parahydrogen into the sample volume under test "S" via capillary tube 60. Indeed, the at least one controller 80 may implement and/or control any suitable aspects and features of the present disclosure.

Figure 4:
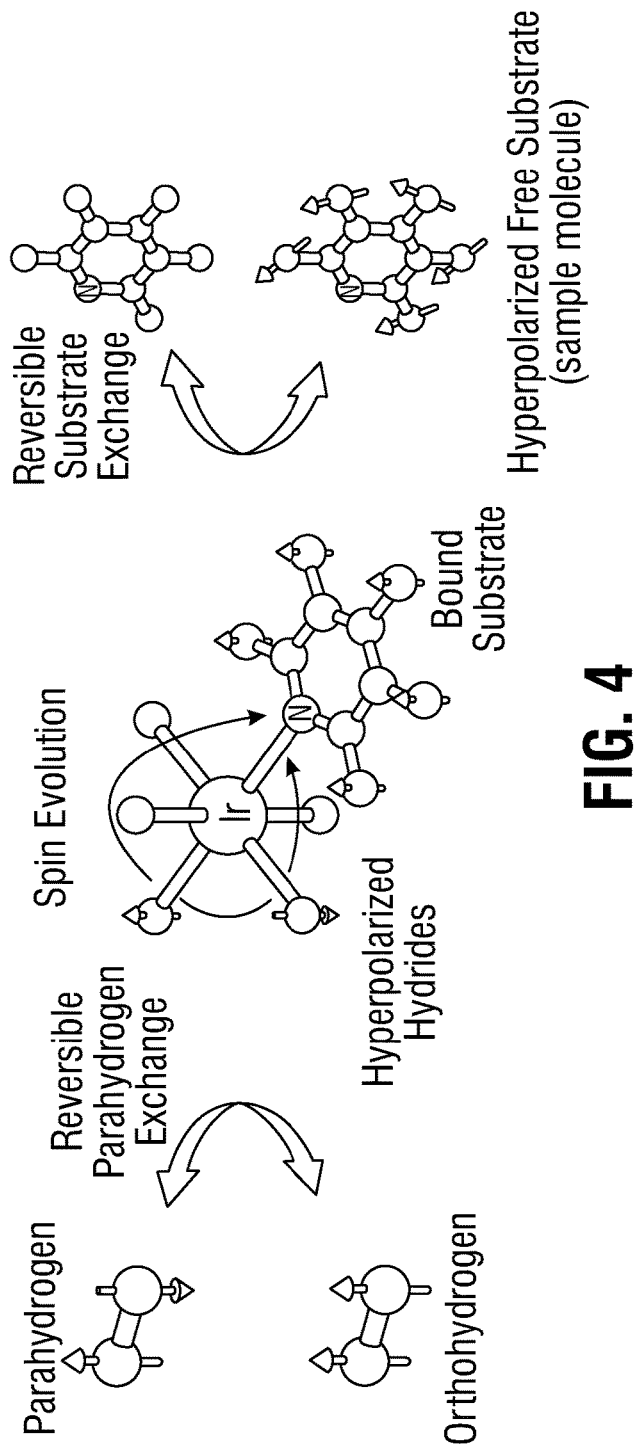
FIG. 4 illustrates the signal amplification by reversible exchange (SABRE) process in accordance with aspects of the present disclosure.
Figure 5:
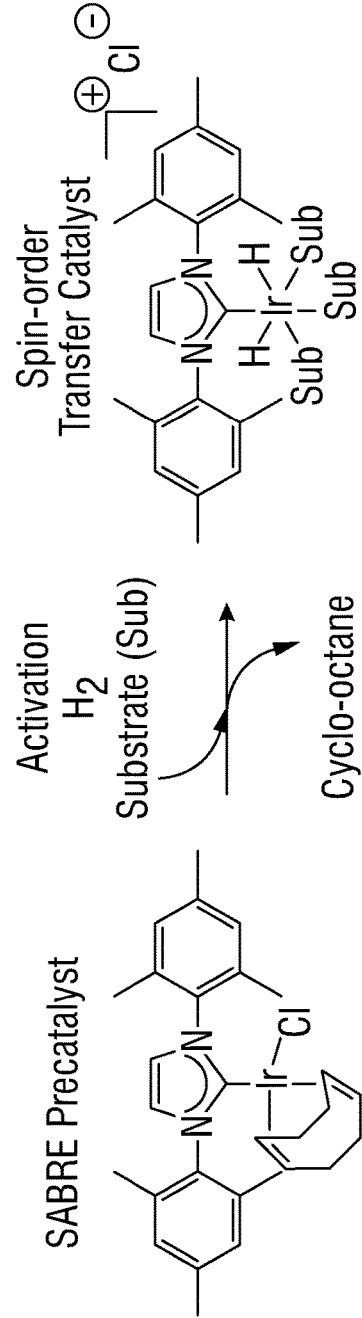
FIG. 5 illustrates the chemical activation of the SABRE catalyst precursor to become the SABRE active spin-order transfer catalyst.

Referring to FIGS. 4 and 5, hyperpolarization of proton spins in the sample volume under test "S" (FIG. 1) is obtained through SABRE. As shown in FIG. 4, the SABRE catalyst is in reversible exchange with parahydrogen (illustrated on left in FIG. 4) and a small molecule substrate (of the sample volume to be tested "S" (FIG. 1), although shown as pyridine for illustration purposes) (illustrated on the right in FIG. 4). In the transient (ms) bound state of the catalyst-substrate complex (illustrated in the center in FIG. 4), spin order flows from the hydrides to the substrate leading to polarization build up on the free substrate in solution (that is, the sample volume under test "S" (FIG. 1)). Although detailed herein with respect to proton spins, it is understood that aspects and features of the present disclosure are also applicable to other ½ nucleus spins such as, for example, nitrogen-15, carbon-13, fluorine-19, phosphorous-31, etc.

More specifically, in implementing SABRE, parahydrogen gas is first dispersed into the sample solution, e.g., the sample volume under test "S" (FIG. 1), for sufficient time, e.g., approximately 20 minutes, to activate an Iridium-based catalyst in the same solution, which mediates reversible exchange of spin order between the parahydrogen and the small molecule substrate in the sample solution. The Iridium-based catalyst may be, for example, [IrCl(COD)(IMes)], COD=1,5-cyclooctadiene; and IMes=1,3-bis (2,4,6-trimethylphenyl)-imidazol-2-ylidene). As illustrated in FIG. 5, the SABRE catalyst precursor is chemically activated by supplying hydrogen gas and substrate. Hydrogen undergoes oxidative addition onto the iridium and the COD (cyclooctadiene) in the catalyst precursor is hydrogenated to cyclooctane. Hence the COD will no longer interact with the catalyst. Instead, the substrate coordinates with the Iridium to form the active spin-order transfer catalyst. Although enriched parahydrogen gas is used to activate the catalyst for convenience, the spin state of the hydrogen gas is irrelevant during the activation process.

Referring back to FIG. 4, after chemical activation of the catalyst as noted above, additional parahydrogen bubbling is provided for sufficient time, e.g., approximately 30 seconds, to establish hyperpolarization on the substrate. That is, the parahydrogen and the small molecule substrate undergo reversible exchange with the catalyst. In the sample solution, e.g., the sample volume under test "S" (FIG. 1), there is free (unbound) hydrogen, free (unbound) substrate, and the SABRE active spin-order transfer catalyst. During the lifetime of the catalyst (on the order of ms), spin-order can flow from parahydrogen to the substrate. Lastly, the hyperpolarized substrate dissociates, to give free hyperpolarized small molecules in solution, e.g., the sample volume under test "S" (FIG. 1), a polarization lifetime of approximately 5 seconds.

The polarization transfer process is resonant at about 6.6 mT, where the J-coupling between the hydrides equals the frequency difference between hydride and substrate proton spins, leading to a level-anti-crossing between the singlet state of the hydrides and the proton spindown states of the substrate. The above-noted reversible exchange process and spin-order transfer act together to continually hyperpolarize the free small molecules in solution, e.g., the sample volume under test "S" (FIG. 1), as long as the parahydrogen is periodically refreshed by bubbling. Thus, as detailed below, the parahydrogen is periodically refreshed by bubbling between sensor measurements obtained by quantum NV-NMR sensor system 10, although it is also contemplated that the parahydrogen may be periodically refreshed at any other suitable interval, e.g., after every N measurements, where N>1.

Figure 6:
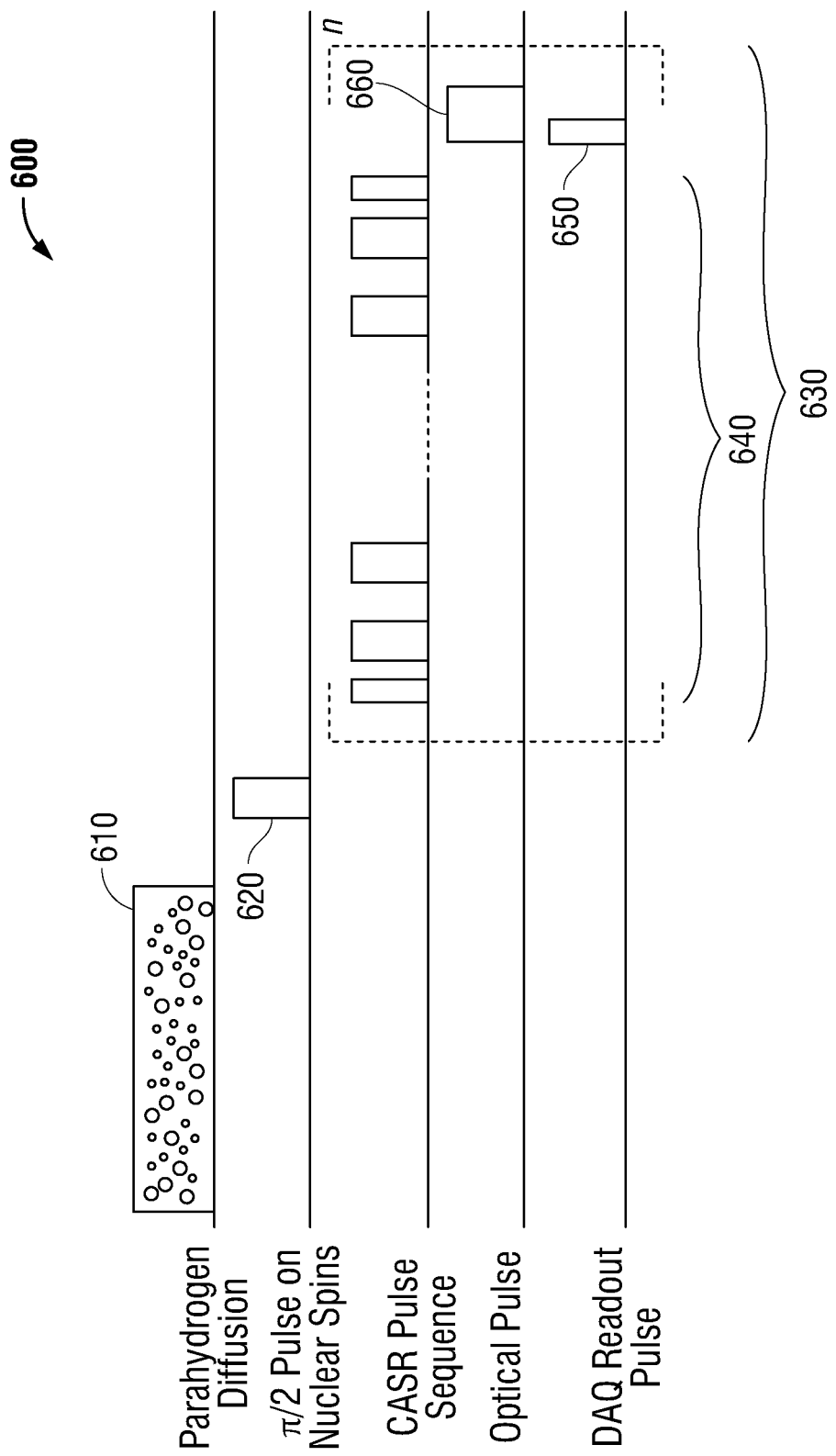
FIG. 6 is a graph illustrating a protocol for quantum NMR sensing in accordance with aspects of the present disclosure.
Figure 7:
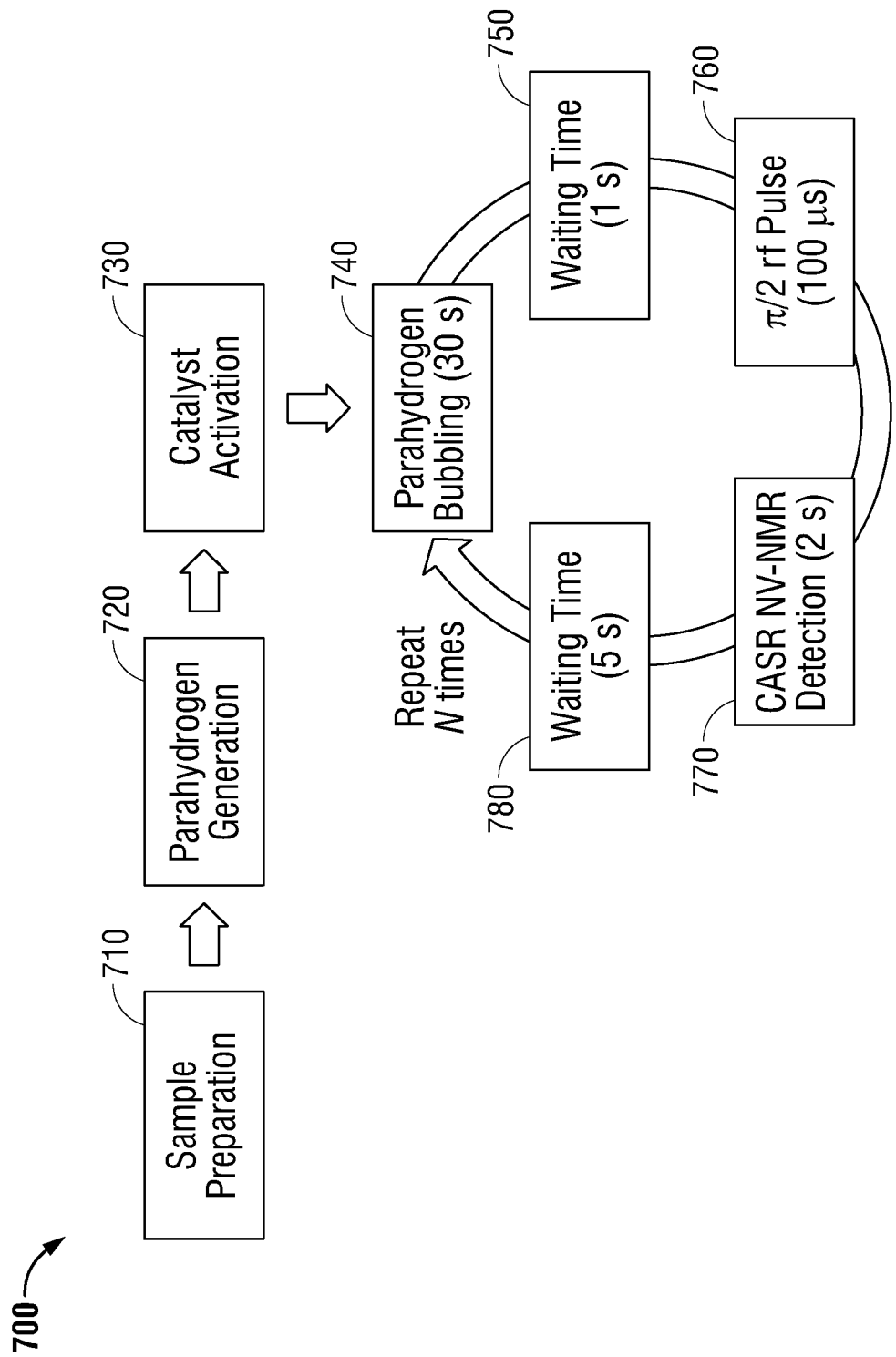
FIG. 7 is a flow diagram of a method provided in accordance with aspects of the present disclosure.

Referring to FIGS. 6 and 7, in conjunction with FIG. 1, a quantum sensing protocol 600 and method 700 in accordance with the present disclosure are described. Protocol 600 and method 700 may be implemented using system 10 (e.g., as controlled by controller 80) or any other suitable system or manner. Further, protocol 600 and method 700 are only exemplary, as it is contemplated that other suitable pulse configurations, sequences, and/or durations may be utilized in accordance with the aspects and features of the present disclosure.

Initially, as indicated at 710, 720, and 730 of method 700, the sample volume to be tested "S" is prepared (e.g., such that the catalyst is introduced therein), the parahydrogen is generated, and chemical activation of the catalyst is performed, respectively, as detailed above. These initialization steps 710-730 are performed prior to the initial sensor measurement to be obtained by quantum NV-NMR sensor system 10.

After the initialization steps 710-730, or for subsequent sensor measurement by quantum NV-NMR sensor system 10 after one or more previous sensor measurements, the parahydrogen is diffused into the sample (parahydrogen bubbling), e.g., via capillary tube 60, as indicated at 610 and 740.

After the parahydrogen bubbling, a wait time may be implemented, e.g., of approximately 1 second, as indicated at 750, to enable the SABRE hyperpolarization. Thereafter, as indicated at 620 and 760, a π/2 RF pulse is applied to the NV center ensemble layer 30 resonant with the nuclear spins of the sample. The induced Larmor precession of the nuclear spin results in a decaying oscillatory magnetic field called free nuclear precession (FNP).

Next, a readout sequence is applied, as indicated at 630 and 770. The readout sequence 630 includes: a CASR pulse sequence 640 implemented to detect the FNP signal and map it onto a population difference of the electronic spin states of the NV center ensemble layer 30; a spin state-dependent fluorescence optical data acquisition (DAQ) readout pulse 650 to read out the population difference; and an optical re-initialization pulse 660 to re-initialize the electronic spin states of the NV center ensemble layer 30. Other suitable readout sequences are also contemplated.

If no further sensor measurements are to be obtained by quantum NV-NMR sensor system 10, protocol 600 and method 700 end. If further sensor measurements are to be obtained by quantum NV-NMR sensor system 10, a wait time may be implemented, e.g., of approximately 5 seconds, as indicated at 780, before method 700 returns to 740 and loops through, repeating protocol 600, N times until all sensor measurements are obtained.

Figure 8:
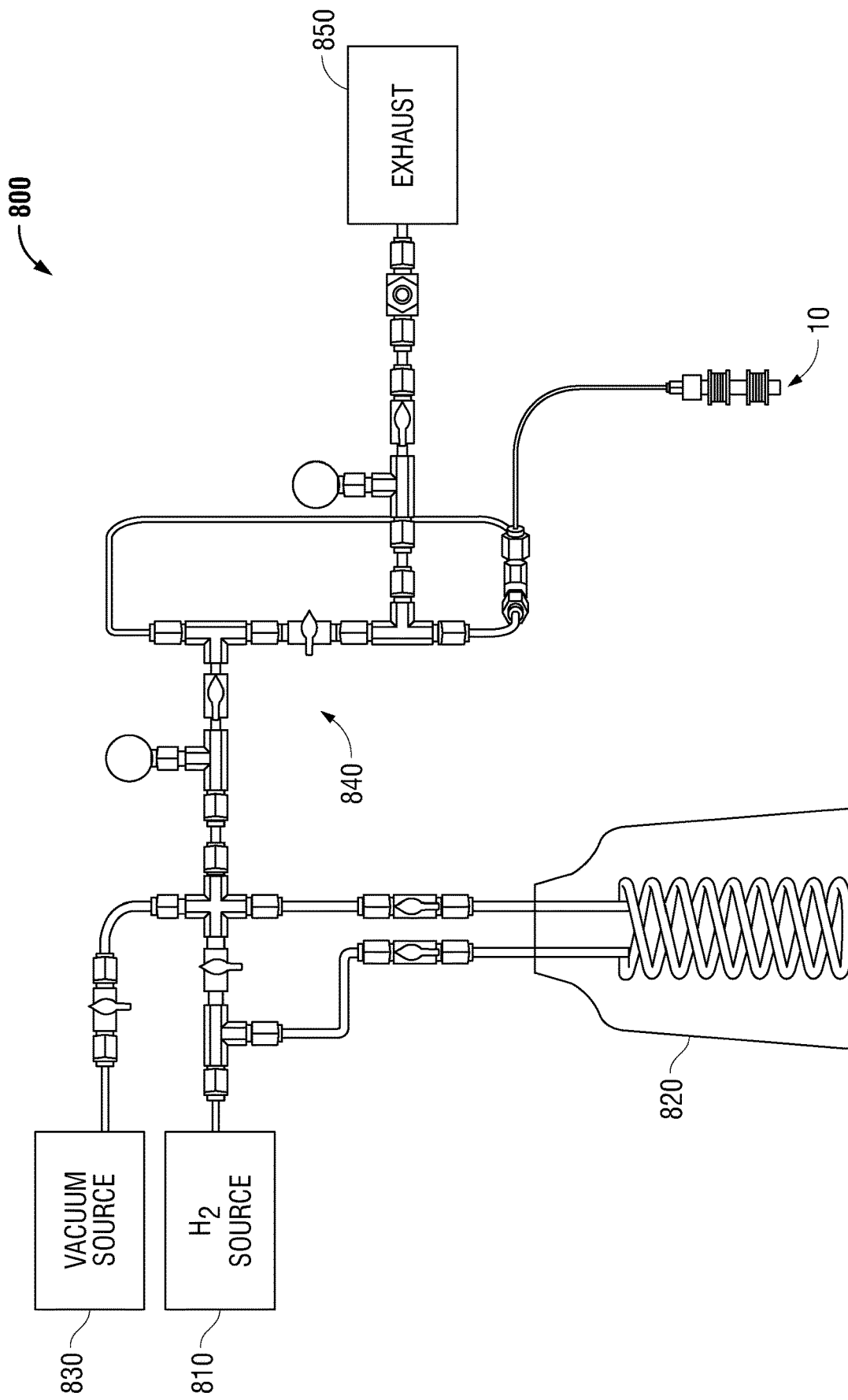
FIG. 8 is a schematic illustration of a system for parahydrogen production for delivery to a quantum NMR sensor in accordance with aspects of the present disclosure.

Turning to FIG. 8, a system 800 configured to produce parahydrogen for use in accordance with the present disclosure is shown. System 800, more specifically, produces parahydrogen by flowing hydrogen gas from a hydrogen gas source 810 through an iron oxide catalyst 820, e.g., at 77 K, aided by vacuum 830. The parahydrogen is then fed through control tubing and valving 840 (having an exhaust 850), to enable bubbling of the parahydrogen through the capillary tube 60 (FIG. 1) and to the sensor 10 where the parahydrogen interacts with the SABRE catalyst to hyperpolarize the sample, as detailed above.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The aspects described with reference to the attached drawings are presented only to demonstrate certain examples of the disclosure. Other elements, steps, methods, and techniques that are insubstantially different from those described above and/or in the appended claims are also intended to be within the scope of the disclosure.

What is claimed is:

1. A method of quantum sensing, comprising:
    depositing a sample volume onto an ensemble of quantum defects;
    hyperpolarizing spins in the sample volume;
    performing a sensing sequence; and
    reading out information regarding electronic spin states of the quantum defects in the ensemble of quantum defects, which sense the hyperpolarized spins in the sample volume.

2. The method according to claim 1, further comprising preparing the sample volume by introducing a catalyst into the sample volume.

3. The method according to claim 2, further comprising dispersing parahydrogen into the sample volume to activate the catalyst.

4. The method according to claim 3, further comprising performing parahydrogen bubbling, wherein the parahydrogen bubbling hyperpolarizes the spins in the sample volume.

5. The method according to claim 1, wherein hyperpolarizing the spins includes performing signal amplification by reversible exchange (SABRE).

6. The method according to claim 1, further comprising applying a magnetic bias field to the ensemble of quantum defects.

7. The method according to claim 1, further comprising applying a radio frequency (RF) pulse to the ensemble of quantum defects after hyperpolarizing the spins and before performing the sensing sequence.

8. The method according to claim 7, wherein the RF pulse is $\pi/2$ RF pulse.

9. The method according to claim 7, further comprising implementing a wait time after hyperpolarizing the spins and before applying the RF pulse.

10. The method according to claim 1, wherein performing the sensing sequence includes performing a coherently averaged synchronized readout (CASR) sequence.

11. The method according to claim 1, wherein reading out the information regarding electronic spin states includes reading out a population difference of the electronic spin states.

12. The method according to claim 1, wherein the ensemble of quantum defects includes a plurality of nitrogen vacancy (NV) centers in diamond.

13. The method according to claim 1, further comprising repeating, a plurality of times: hyperpolarizing the spins in the sample volume, performing the sensing sequence, and reading out the information regarding the electronic spin states.

14. The method according to claim 13, further comprising implementing a wait time after reading out the information regarding the electronic spin states and before repeating hyperpolarizing the spins in the sample volume.

15. The method according to claim 1, further comprising, after reading out the information regarding electronic spin states, re-initializing the electronic spin states of the quantum defects.

16. The method according to claim 1, wherein re-initializing includes applying an optical re-initialization pulse to the ensemble of quantum defects.

17. A quantum sensing system, comprising:
an ensemble of quantum defects configured to receive a sample volume thereon;
a tube configured to deliver parahydrogen to the sample volume to hyperpolarize spins in the sample volume;
a laser source configured to deliver a sensing sequence of light pulses to the ensemble of quantum defects; and
a sensor configured to read out information regarding electronic spin states of the quantum defects in the ensemble of quantum defects, which sense the hyperpolarized spins in the sample volume.

18. The quantum sensing system according to claim 17, further comprising an antenna configured to deliver radio frequency (RF) pulses to the ensemble of quantum defects.

19. The quantum sensing system according to claim 17, wherein the ensemble of quantum defects includes a plurality of nitrogen vacancy (NV) centers in diamond.

20. The quantum sensing system according to claim 17, further comprising a controller including at least one processor and at least one associated memory storing instructions to be executed by the at least one processor to cause the at least one controller to repeatedly:
direct the delivery of parahydrogen to the sample volume via the tube;
direct the laser source to deliver the sensing sequence of light pulses to the ensemble of quantum defects; and
obtain, from the sensor, the read out information regarding the electronic spin states of the quantum defects in the ensemble of quantum defects.

21. A method of quantum sensing, comprising:
providing an ensemble of quantum defects having a sample volume deposited on the ensemble of quantum defects, wherein spins in the sample volume are hyperpolarized; and
performing a quantum sensing protocol to read out information regarding electronic spin states of the quantum defects in the ensemble of quantum defects, which sense the hyperpolarized spins in the sample volume.

22. The method according to claim 21, wherein the quantum sensing protocol includes a sensing sequence.

23. The method according to claim 22, wherein the sensing sequence includes a coherently averaged synchronized readout (CASR) sequence.

24. The method according to claim 21, wherein the quantum sensing protocol includes a read out pulse.

25. The method according to claim 24, wherein the read out pulse reads out a population difference of the electronic spin states of the quantum defects in the ensemble of quantum defects.

26. The method according to claim 21, wherein providing the ensemble of quantum defects having the sample volume deposited on the ensemble of quantum defects includes:
depositing the sample volume on the ensemble of quantum defects; and
hyperpolarizing the spins in the sample volume deposited on the ensemble of quantum defects.

27. The method according to claim 21, further comprising, repeating at least once after performing the quantum sensing protocol:
hyperpolarizing the spins in the sample volume; and
performing the quantum sensing protocol again.

28. The method according to claim 27, further comprising, for each repeat, re-initializing the electronic spin states of the quantum defects after a prior quantum sensing protocol and before a next hyperpolarizing.

* * * * *